(12) United States Patent
Boehm et al.

(10) Patent No.: US 9,427,290 B2
(45) Date of Patent: Aug. 30, 2016

(54) DISPENSING DEVICE FOR A DENTAL SUBSTANCE

(75) Inventors: Andreas Johannes Boehm, Reichling (DE); Marc Peuker, Schondorf (DE); Alexander Walter, Pürgen (DE); Peter Müller, Herrsching (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/264,809

(22) PCT Filed: Apr. 19, 2010

(86) PCT No.: PCT/US2010/031561
§ 371 (c)(1),
(2), (4) Date: Nov. 30, 2011

(87) PCT Pub. No.: WO2010/123800
PCT Pub. Date: Oct. 28, 2010

(65) Prior Publication Data
US 2012/0064482 A1   Mar. 15, 2012

(30) Foreign Application Priority Data

Apr. 23, 2009   (GB) .................................. 0906925.3

(51) Int. Cl.
A61C 5/04   (2006.01)
A61C 5/06   (2006.01)

(52) U.S. Cl.
CPC ..................................... *A61C 5/062* (2013.01)

(58) Field of Classification Search
CPC .... A61C 9/0026; A61C 5/062; A61C 5/064; A61C 5/06; A61C 8/0018; A61C 8/0022; B65D 47/30
USPC .......... 433/80, 83, 87, 89, 90; 222/526–533, 222/153.01–153.04, 153.09–153.14, 222/320–322, 505, 145.2, 536; 604/82, 83, 604/236, 246–248, 256, 258, 310, 311; 137/616–616.7; 251/149.2, 149.9, 251/89.5, 304–317.01
See application file for complete search history.

(56) References Cited

U.S. PATENT DOCUMENTS 4,993,948 A * 2/1991 Cameron et al. ................ 433/90
5,050,841 A * 9/1991 Jacobsson ............... F16L 37/47
                                              251/149.9

(Continued)

FOREIGN PATENT DOCUMENTS

CN   1835873 A    9/2006
DE   199 61 485   7/2001

(Continued)

OTHER PUBLICATIONS

International Search Report for International Patent Application No. PCT/US2010/031561, dated Jul. 30, 2010.

*Primary Examiner* — Cris L Rodriguez
*Assistant Examiner* — Mirayda A Aponte

(57) ABSTRACT

A dispensing device for a dental substance is provided which has an outlet for the dental substance, and a valve for opening and closing the outlet. The device is switchable between a storage mode and an operative mode. In the storage mode a cannula is locked in the device and the valve opens the outlet, and in the storage mode the cannula can be released from the device and the valve closes the outlet. The device may facilitate handling and may be relatively inexpensive.

16 Claims, 11 Drawing Sheets

(56) References Cited

U.S. PATENT DOCUMENTS

| | | | |
|---|---|---|---|
| 5,562,273 A * | 10/1996 | Wuethrich | F16L 37/47 |
| | | | 137/616.7 |
| 5,722,830 A * | 3/1998 | Brandhorst et al. | 433/90 |
| 6,375,460 B1 * | 4/2002 | Plaumann | 433/80 |
| 7,198,619 B2 * | 4/2007 | Bills et al. | 604/218 |
| 2005/0202365 A1 * | 9/2005 | Cao et al. | 433/89 |
| 2006/0105292 A1 * | 5/2006 | Dorsey et al. | 433/90 |
| 2007/0015106 A1 | 1/2007 | Bertl | |
| 2007/0164047 A1 * | 7/2007 | Reidt | A61C 5/064 |
| | | | 222/137 |
| 2007/0166660 A1 * | 7/2007 | Peuker et al. | 433/89 |
| 2008/0287880 A1 | 11/2008 | Keller | |
| 2009/0298010 A1 * | 12/2009 | Broyles et al. | 433/90 |

FOREIGN PATENT DOCUMENTS

| | | |
|---|---|---|
| FR | 2 898 112 | 9/2007 |
| SU | 705266 | 12/1979 |
| WO | WO 2005/016783 | 2/2005 |
| WO | WO 2006/005206 | 1/2006 |
| WO | WO 2007/104037 | 9/2007 |
| WO | WO 2010/123800 | 10/2010 |

* cited by examiner

DISPENSING DEVICE FOR A DENTAL SUBSTANCE

CROSS REFERENCE TO RELATED APPLICATIONS

This application is a national stage filing under 35 U.S.C. 371 of PCT/US2010/031561, filed Apr. 19, 2010, which claims priority to Great Britain Application No. 0906925.3, filed Apr. 23, 2009, the disclosures of which are incorporated by reference in their entirety herein.

FIELD OF THE INVENTION

The invention relates to a dispensing device for a dental substance, in particular to a dispensing device that is switchable between a storage mode and a use mode, and which can be used with a replaceable cannula.

BACKGROUND OF THE INVENTION

Dental substances are often provided in packages holding a sufficient amount of substance for multiple applications. A dentist typically uses portions of such substances for application in a patient's mouth. A dentist may for example place a portion of a dental substance on a pad or into a well and use a dental instrument for applying it within a patient's mouth. Dental impression materials may for example be filled into a dental impression tray which is then placed in a patient's mouth to obtain a dental impression from the patient's teeth. However in many situations dental substances may also be placed into a patient's mouth directly from a package in which the substance is contained. Today there are a variety of packages that allow for direct application of substances into a patient's mouth.

Dental substances further are often prepared from two or more components that are mixed together just before use. Often the individual components are obtained as portions from larger packages, for example from tubes, bags or cartridges. There are packages on the market that allow manual or automatic dispensing of two or more components at desired amounts and at an appropriate ratio for mixing. Furthermore there are packages that allow dispensation of portions of readily mixed substances from individually stored components.

An automatic dispensing and mixing system is for example available under the designation 3M™ ESPE™ Pentamix™ from 3M ESPE AG, Germany, and allows automatic dispensing and mixing of two-component dental impression materials. The 3M™ ESPE™ Pentamix™ system is typically used as a tabletop device for filling dental impression trays. However, the 3M™ ESPE™ Pentamix™ system further has an interface which allows a hand-held syringe to be filled with a portion of a readily mixed dental substance. A re-usable syringe for use with the 3M™ ESPE™ Pentamix™ system is for example available under the designation Elastomer Syringe from 3M ESPE AG, Germany.

A manual dispensing device is available under the designation 3M™ ESPE™ Garant™ Dispenser from 3M ESPE AG, Germany, and it allows manual dispensing of two-component substances through a static mixer so that a readily mixed substance can be obtained. The 3M™ ESPE™ Garant™ Dispenser allows direct application of the mixed substance into a patient's mouth because it is provided in the form of a hand-held applicator which carries the dental impression material, and it includes a mixing tip. The mixing tip is dimensioned so that it can be placed even in relatively narrow spaces in a patient's mouth.

WO 2007/104037 discloses another dispensing device for storing and dispensing dental substances. The device comprises a cartridge for the dental substance, and a nozzle. The nozzle is pivotable with respect to the cartridge between a first position in which the capsule is closed for storage and a second position in which the capsule is opened for dispensing the dental substance.

Although there are a variety of solutions for application of dental substances into a patient's mouth there is still a desire for an application device that allows easy handling, and which is relatively inexpensive.

SUMMARY OF THE INVENTION

The invention relates to a dispensing device for a dental substance. The dispensing device comprises an outlet for the dental substance, and a valve for opening and closing the outlet. The device is operable between a storage mode and an operative mode, and is adapted for receiving a cannula for connection with the outlet.

The device is in a first alternative adapted such that in the operative mode the valve opens the outlet, and the cannula, when it is present, is locked in the device.

The device is in a second alternative adapted such that in the storage mode the valve closes the outlet, and the cannula, when it is present, is released from the device.

The device may further be adapted such that in the operative mode the valve opens the outlet, and the cannula, when it is present, is locked in the device, and such that in the storage mode the valve closes the outlet, and the cannula, when it is present, is released from the device.

In particular the device may be adapted such that activating the operative mode causes the valve to open the outlet, and locking the cannula, when it is present, in the device. And the device may be adapted such that activating the storage mode causes the valve to close the outlet, and releasing the cannula, when it is present, from the device.

For the purpose of this invention "locking" preferably involves a form fit or positive lock of at least two parts.

The device of the invention may be advantageous in that it may help keep the dental substances encapsulated even when the cannula is removed from the device. For example a user of the device may only be enabled to remove the cannula in the storage mode, in which the outlet is closed. The substances may thus be enclosed within the device. Therefore the device may be advantageously usable in combination with substances that are sensitive to moisture, air and/or light. The device may thus be advantageous for storing substances over a certain storage time. The device may allow a cannula to be replaced by a fresh cannula once the device was used. Thus the device may help in fulfilling relatively strict hygiene requirements because it may allow a fresh cannula to be used for each use, for example if different patients are to be treated with the same device. Further the device may be used as a package containing multiple doses of two- or multi-component substances, for example hardenable substances. In that case the individual components of the substance may be co-dispensed and mixed in the cannula. The device of the invention may enable the cannula, which after use typically gets blocked when the mixed substances harden, to be replaced by a fresh one for the next use. The device may further provide for a cannula design having a minimum size and a minimum number of parts. Therefore waste may be minimized, in particular in view of disposal of exchangeable cannulas. The device thus may be relatively environmentally compatible and may help to save costs for the user. Further the device may be generally light weight, and/or may provide for a relatively convenient handling.

Preferably the dispensing device comprises a container for receiving the dental substance. The device may further comprise a piston for urging the dental substance toward the outlet. The piston is preferably movable along a longitudinal axis of the device within the container. Preferably the container has a chamber for receiving the substance. The chamber may extend along the longitudinal axis of the device with a generally uniform, for example circular, oval, or D-shaped cross-section over at least part of its length. Further the chamber preferably opens into the outlet. The piston may be adapted to sealingly fit within the chamber, preferably on the opposite end from the outlet, and may be movable along the longitudinal axis of the device within the chamber. The piston may be connected to a plunger, or may be part of a plunger. The plunger may have a pressure plate. The pressure plate may allow for manual advancing the plunger relatively conveniently, for example by a user's thumb or finger. However the piston or plunger may also be adapted for advancement by a separate manual or powered applicator.

In one embodiment the container has at least two chambers. Each of the chambers may be provided for receiving at least one component of a dental substance. The chambers may each extend along the longitudinal axis with a generally uniform cross-section. Further the cross-sectional areas may be dimensioned to provide a ratio of 1:1, 1:2, 1:4, 1:5 or 1:10, for example. Each of the chambers may open into an outlet. The device of this embodiment may further have a plunger that comprises two pistons being receivable in the chambers, respectively, for extruding the dental substance from the chamber. The pistons are preferably receivable at an end of the chambers opposite the outlets. In this embodiment of the invention the plunger may have a common pressure plate for simultaneously advancing the pistons by advancing the pressure plate. The plunger, the pistons and the pressure plate may form a single piece, for example an integrally formed piece. This embodiment of the device of the invention may allow for dispensing of two individual components from the device. For example the device may be used to dispense two components of a substance which when mixed together chemically react, for example harden. With the device of the present invention such mutually reacting components may be kept separate in the device until they are dispensed from the device. Therefore the storage time of the stored components may be enhanced relative to a mixture of the same components.

In another embodiment the dispensing device has at least two fingerplates which are arranged along the longitudinal axis of the device and spaced from one another. A device having two fingerplates is for example disclosed in co-pending UK patent application no. 0902354.0 which is incorporated by reference herein. The two fingerplates may allow for more convenient handling of the device. For example when the device is filled with a substance and therefore the plunger is retracted, the distance between the pressure plate and a first finger plate may be arranged for manual advancement of the piston by a user. However at a stage where some of the substance stored in the device has been dispensed from the device the distance between the pressure plate and a first finger plate has typically been reduced and therefore may be less convenient. In this case the user may change from the first to a second fingerplate which is further remote from the pressure plate. With the distance between the second fingerplate and the pressure plate being increased relative to the distance between the first fingerplate and the pressure plate, more effective handling may be provided.

In a further embodiment the dispensing device may have a coupling for connecting a package containing at least two components of a dental substance with the chambers, such that each chamber can be filled by an individual component. The coupling may for example comprise two inlet nozzles for connecting with respective outlet nozzles of the package. The package may be adapted such that a component can be dispensed through each outlet nozzle. Thus the each of the chambers may be filled with an individual component from the package. An embodiment of such device is also disclosed in the UK patent application no. 0902354.0 which particularly is incorporated by reference herein. The device of the invention therefore may be refillable and therefore reusable. This may also help to save costs, for example relative to single use devices.

The device may contain a dental substance selected from among a dental filling material, a dental impression material, a dental sealant, and a dental adhesive, for example.

In another embodiment the dispensing device of the invention, is in combination with an applicator for dispensing the dental substance from the device. An applicator as it may be used with the present invention is for example available under the designation 3M™ ESPE™ Capsule Dispenser from 3M ESPE AG, Germany.

In one embodiment the dispensing device comprises a valve body. The valve body may be part of the container, in particular the valve body may be integrally formed with the container. The valve body may comprise the outlet(s) of the device and may receive a valve element. Therefore the valve may be part of the dispensing device. Further the valve may not be part of the cannula, for example. The valve element preferably comprises a sealing surface for sealing with the valve body and at least one conduit. The valve element may comprise two or more conduits in embodiments of the device having two or more outlets. However in a preferred embodiment the valve element may have a conduit which is at least over a section shaped to connect with two or more outlets. For example the conduit may have a funnel shaped section with the funnel opening being sized to surround at least two outlets. The conduit may further comprise two or more conduit sections which within the valve element merge into a common conduit section.

The valve body and the valve element are preferably movable relative to one another between an open position, in which the conduit is in fluid communication with the outlet(s) so that the outlet(s) is/are open, and a closed position, in which the sealing surface cover(s) or seal(s) the outlet(s) so that the outlet(s) is/are closed. The valve element may have a generally cylindrical outer surface, and the valve body may have a corresponding generally cylindrical inner surface. The outer surface of the valve element and the inner surface of the valve body are preferably mated with one another, such that the valve body and the valve element are rotatable relative to one another around a rotation axis.

In one embodiment of the invention the rotation axis is generally transverse to the longitudinal axis of the device. In another embodiment the rotation axis may be generally parallel to or aligned with the longitudinal axis of the device. Further the rotation axis may be inclined relative to the longitudinal axis, for example may be arranged at any angle between transverse to and aligned with the longitudinal axis.

In one embodiment at least part of the outer surface of the valve element may form the sealing surface. The sealing surface may further be arranged on a face side of the valve element which is generally transverse to the rotation axis.

Any arrangement of the sealing surface may be used with any orientation of the rotation axis relative to the longitudinal axis of the device.

An embodiment of the device may have at least two valves, or at least two valve elements in a common valve body. Each of the valves or valve elements may cooperate with one or more different outlets of the device. Such a device may also have two or more valves according to different embodiments as described herein.

In another embodiment the valve element is adapted to receive an end of the cannula such that the cannula is in fluid communication with the conduit. Therefore in the open stage of the device the outlet(s) may be in fluid communication with the conduit and the conduit may be in fluid communication with the cannula. Thus the cannula may be connected to the outlet(s) of the device, and substance(s) dispensed from the outlet(s) may be guided through the conduit into the cannula.

In an embodiment the dispensing device comprises the cannula. The cannula may for example be connected to the device. Further the container may have a retainer, and the cannula may have a retention element. The retention element may be part of the cannula or part of a separate element that forms an adapter for locking the cannula to the device. The skilled person may appreciate different possibilities of indirectly connecting the retention element to the cannula in, for example by one or more adapters. Although in the following it may be generally referred to a retention element as part of the cannula, an indirect connection between the retention element and the cannula shall be included.

Preferably the retainer and the retention element are adapted to cooperate for locking the cannula in the device. The retainer and the retention element may be movable relative to one another. In particular the cannula (or an adaptor) that may carry the retention element may be movably connected to the device which may carry the retainer. The retainer and the retention element may be movable relative to one another between a first and a second position. A move from the first to the second position of the retainer relative to the retention element may cause locking the cannula and the opposite move may cause unlocking the cannula. The cannula is preferably only releasable when it is unlocked. In particular "unlocking" preferably results in the cannula to remain received in the device, but renders the cannula releasable relative to the cannula when locked. This may facilitate locking and unlocking of the cannula because it may be pre-fixed in the device.

In the first position of the retainer relative to the retention element the retention elements may be disengaged from the retainers, and in the second position of the retainer relative to the retention element the retaining elements may be engaged with the retainers. The retention element may be formed by an annular rim, for example a rim that is arranged adjacent a backend of the cannula. The retention element may further be formed by at least one wing projecting sideward from the cannula. Other structures are possible, like a pin, or a thread for example.

In another embodiment the cannula has a socket for receiving a front end of the container. In this embodiment the retention element may be arranged in the socket, for example at an inner side wall of the socket. The retainer of the device may in this embodiment be arranged at an outer side wall of the container. The socket may be a part of the cannula or a separate part forming an adapter to lock the cannula at the device.

The cannula (or an adapter) with the backend may engage the valve element or the valve body such that moving the cannula also causes moving the valve and the valve body relative to one another.

In an embodiment the cannula comprises a static mixer. Therefore two or more components co-extruded through the cannula may be mixed so that a mixture of the components is dispensed from the device.

The invention further relates to a kit of parts. The kit comprises a plurality of cannulas and at least one device according the invention. The kit may further comprise a dental applicator for receiving a device according the invention. The kit may further comprise at least two different types of cannulas, for example cannulas having different lengths, and/or different inner diameters, and/or different mixers with different amounts of mixing paddles. The kit may further comprise at least one package with a dental substance.

DETAILED DESCRIPTION OF THE INVENTION

Figure 1:
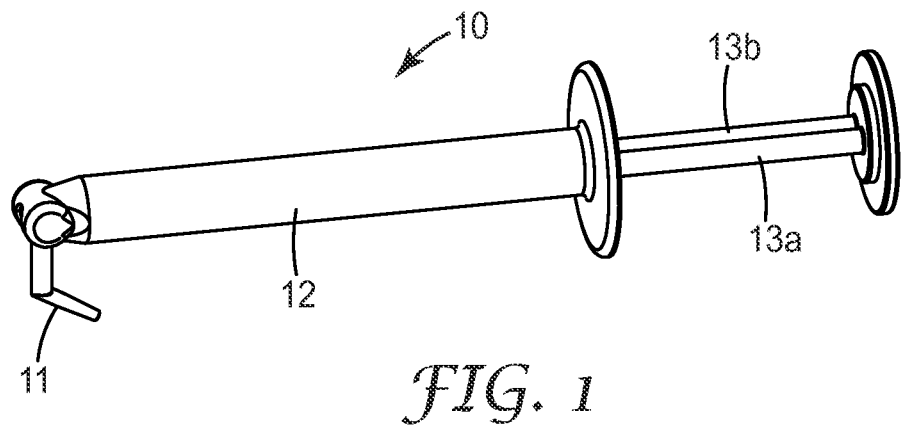
FIG. 1 is a perspective view of a dispensing device in the storage mode according to an embodiment of the invention.

FIG. 1 shows an embodiment of the dispensing device 10 of the invention in the storage mode. The device is shown with a cannula 11 received at the device. In the illustrated storage mode the cannula 11 is releasably mounted at the device. Therefore this mode of the device allows for removing and/or replacing the cannula 11, for example by a user. The device further has a container 12 which has two chambers for containing two components of a dental substance (not shown) and pistons 13a, 13b placed in the chambers. The pistons 13a, 13b are movable within the chambers for extruding the dental substance from the chambers toward an outlet. Further a valve (not shown) closes the outlet of the device in the storage mode.

Although the example shows the device 10 having two chambers with two pistons, the skilled person will appreciate that a device having only one chamber with one piston, or a device having multiple chambers with multiple pistons may likewise be used with the present invention.

Figure 2:
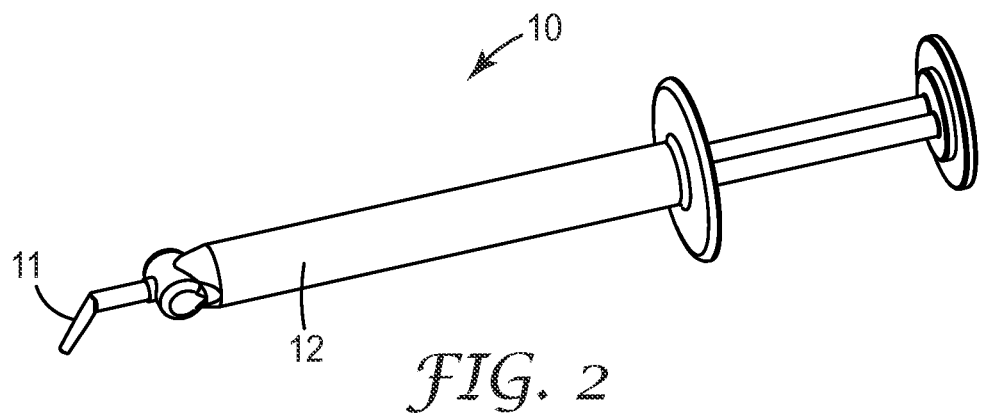
FIG. 2 is a perspective view of the dispensing device of FIG. 1 in the operative mode according to an embodiment of the invention.

FIG. 2 shows the device 10 in an operative mode. In the operative mode the valve is open to the outlet and thereby further preferably establishes a fluid communication between the outlet and the cannula 11. Thus in the operative mode the device 10 can be used to extrude substance from the container 12 through the cannula 11. In the operative mode the cannula 11 is locked in the device 10 such that it is prevented from being removed, for example by a user, from the device. In the operative mode the cannula 11 is particularly locked in the device 10 such that it cannot detach from the device, for example due to forces resulting from urging of substance through the cannula 11. Several embodiments of the device, as it is illustrated in FIGS. 1 and 2 by way of example only, are described below.

Figure 3:
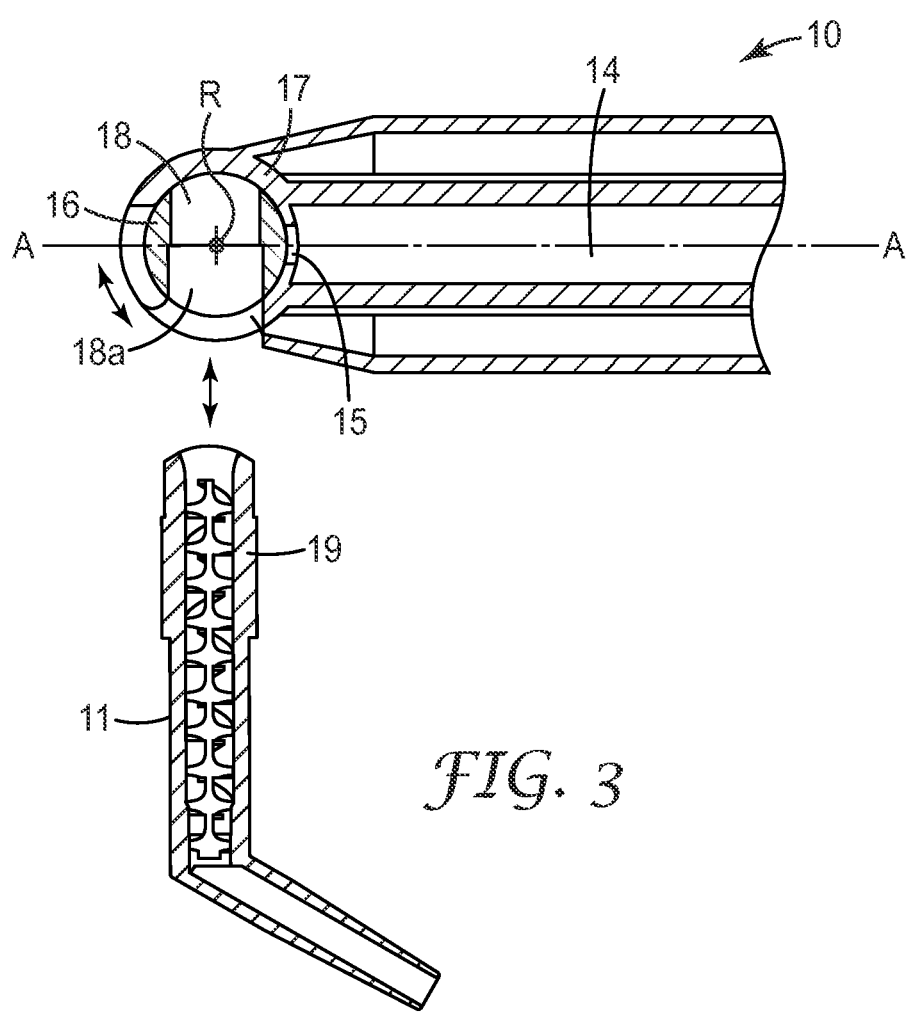
FIG. 3 is a partial cross-sectional view of the device of FIG. 1 with a cannula disconnected from the device according to an embodiment of the invention.

FIG. 3 is a cross-sectional view of a front portion of the device 10 in the storage mode. The cannula 11 is shown separately from the device 10. The device 10 has a chamber 14 along a longitudinal axis A which opens into outlet 15. The chamber 14 may be closed by a piston (not shown) received in the chamber 14 opposite of the outlet 15. A valve element 16 and a valve body 17 together form a valve which in the illustrated storage mode closes or seals the outlet 15. The valve element 16 and the valve body 17 are rotatable relative to one another. The rotation axis R (orthogonally to the plane of the Figure) of the valve element 16 relative to the valve body 17 in this example is arranged transverse to the longitudinal axis A of the chamber 14. This arrangement allows relatively good sealing of the outlet by the valve element if a press fit between the valve element and the valve body is provided because due to the press fit the valve element may be pressed against the outlet tightly and therefore provide a good seal for the outlet. Such a press fit may be achieved by providing an oversize of the valve element with respect to the size of the valve body, which further can be manufactured relatively easily and relatively inexpensively. For example the valve element and the valve body may be manufactured by two-shot injection molding. Particularly the valve element may be pre-molded and subsequently overmolded to form the valve body. Thus the valve body during solidifying may shrink onto the already solidified valve element such that a press fit is formed.

The valve element 16 in the example has a conduit 18. In the example shown the conduit has a widened portion 18a which is adapted to receive the backend 19 of the cannula 11. The transition between the conduit 18 and the widened portion 18a in the example forms a step which the backend 19 of cannula 11 abuts when inserted in the widened portion. Therefore the cannula can be positioned in the device relatively conveniently when inserted in the device. The conduit may instead have a uniform cross-section without a widened portion which, for example may facilitate manufacturing. In another example the conduit may have a constricted portion for receiving the cannula, for example to receive a cannula of a smaller size. The cross-sections of the conduit 18, particularly of the widened portion 18a, and the backend 19 of the cannula 11 may be shaped and sized to allow the backend 19 to be inserted into the conduit 18 (or widened portion 18a). Thus a plug and socket connection may be formed. For example the cross-sections of the conduit 18 (or widened portion 18a) and the backend 19 of the cannula 11 may generally correspond in size and shape to one another so that they can be mated. Although not shown, the skilled person will appreciate other configurations for mating the cannula and the valve, like for example with the socket arranged at the cannula and the corresponding plug at the valve element.

Figure 4:
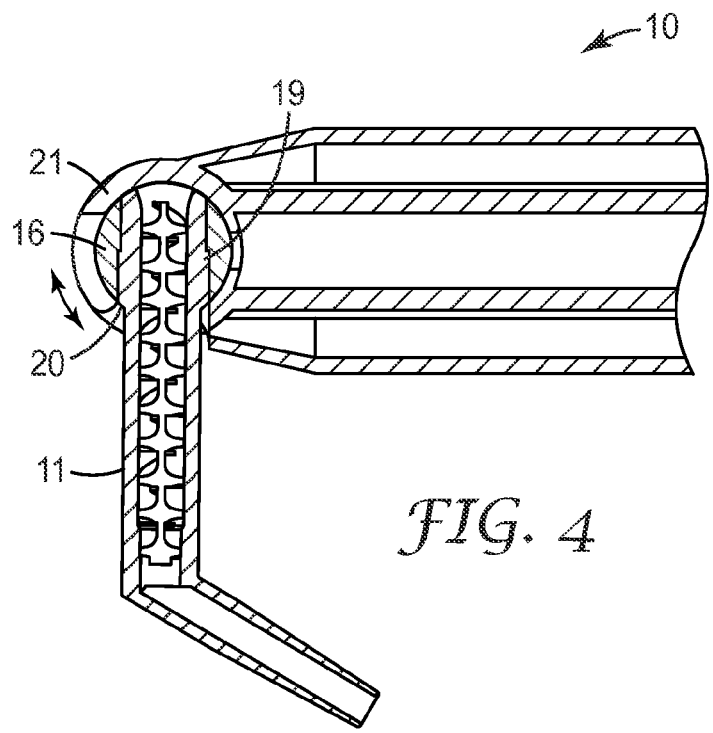
FIG. 4 is a partial cross-sectional view of the device of FIG. 1 with the cannula connected to the device and the device in the storage mode according to an embodiment of the invention.

FIG. 4 shows the device 10 in the storage mode, but with the cannula 11 received in the conduit 18 of the valve element 16. The backend 19 of the cannula 11 in the example is provided with a retention element 20. In the example shown the retention element is formed by a step between a widened cross-section at the cannula backend 19 and the remainder of the cannula 11. The backend 19 may for example have an annular rim of a larger diameter than at least a section of the cannula further to the frontend, or the cannula may at the backend 19 have at least one, preferably two, laterally protruding pins or wings, or similar structures.

In the storage mode of the device as shown in FIG. 4 the retention element 20 of the cannula 11 is disengaged from a retainer 21 of the device so that the cannula 11 is releasable or removable from the device 10. The cannula 11 may nevertheless be releasably retained also in the storage mode of the device, for example by a snug fit or snap fit between the cannula backend 19 and the conduit 18. Thus in the storage mode the cannula 11 may be sufficiently retained in the device so that it is hindered from detaching just due to handling of the device, but may be detached at relatively low forces, for example by a user. This may provide for a more convenient handling of the device.

Figure 5:
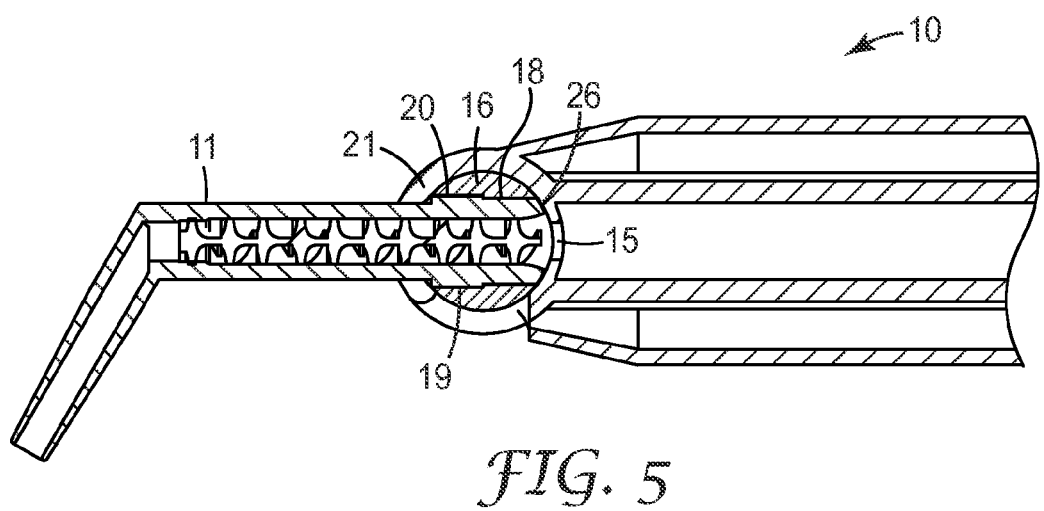
FIG. 5 is a partial cross-sectional view of the device of FIG. 1 with the device in the operational mode according to an embodiment of the invention.

In FIG. 5 the device 10 is shown with the cannula 11 and the valve element 16 (as well as the cannula 11) positioned about 90° clockwise relative to FIG. 4. This may be achieved by rotating the cannula 11, which causes the valve element 16 to rotate and therefore also causes the valve to open the outlet 15. In this position the retention element 20 of the cannula 11 is in engagement with the retainer 21 of the device 10. The cannula 11, particularly the retention element 20, further abuts the step formed in the conduit 18. Therefore the cannula 11 is locked between the step in the conduit 18 and the retainer 21. In an embodiment having a conduit of generally uniform cross-section the cannula may abut at an inner surface of the valve body instead at the step, thus being locked between the valve body and the retainer of the device.

The cannula 11 may have a seal 26 (indicated by reference number but not illustrated) at the backend 19 which is adapted to provide a seal between the outlet 15 and the cannula 11. In the example the cannula 11 and the valve element 16 are configured such that the cannula backend 19 can extend entirely through the valve element 16. Thus the seal 26 can contact the inner surface of the valve body 17 and in the operative position provide a seal between the outlet 15 and the cannula 11. Therefore replacing the cannula by a fresh cannula also provides a fresh seal. The seal may also provide a wiping effect when the valve element and the valve body are moved relative to one another. For example the seal may wipe off substance from the outlet and wipe over the inner surface of the valve body when the valve is closed and therefore prevent substance to be carried between the valve element and the valve body. Leakage of the device between the cannula and the outlet may therefore be prevented even when the device is used multiple times.

The retention element 20, and the retainer 21 together preferably form a positive fit. The retention in the operative mode, particularly the retention provided or contributed by the cooperating retention element 20 and retainer 21 is preferably higher than a retention possibly provided in the storage mode. The retention in the operative mode preferably at least compensates forces on the cannula resulting from extruding substance through the cannula.

Figure 6:
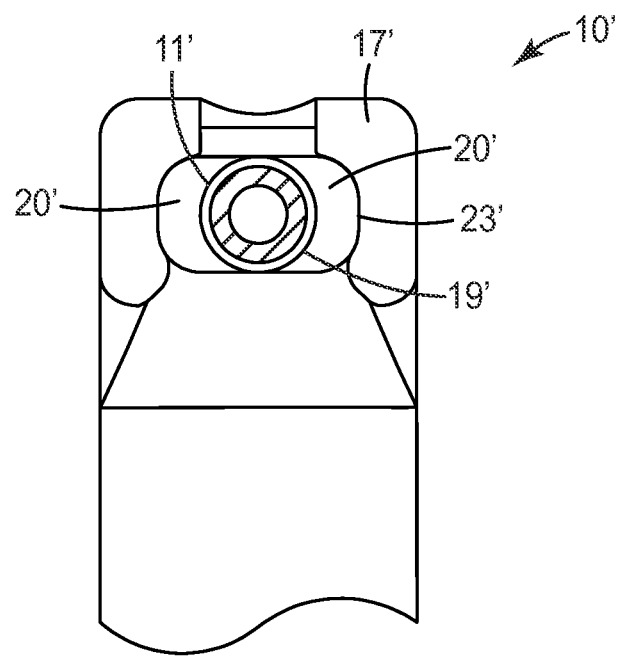
FIG. 6 is a partial bottom view of another device in the storage mode according an embodiment of the invention.

FIG. 6 is a bottom view of a device 10' in the storage mode. The device 10' corresponds to the device 10 shown in FIGS. 3 to 5, but only varies in that the device 10' is adapted to cooperate with a cannula 11' having a retention element 20' of a different shape. The cannula 11' has laterally protruding wings that form retention elements 20'. The valve body 17' is recessed to provide an open window 23' that is wide enough to allow the cannula backend 19' including the retention elements 20' to be passed through. Thus the cannula backend 19' can be moved into and removed from the device 10' through the window 23'.

The window 23' further extends towards the front of the device 10' (in the Figure further to the top) so that the cannula 11', which extends through the window 23', is enabled to be moved within the window 23' for switching the device 11' from the storage mode into the operative mode.

Figure 7:
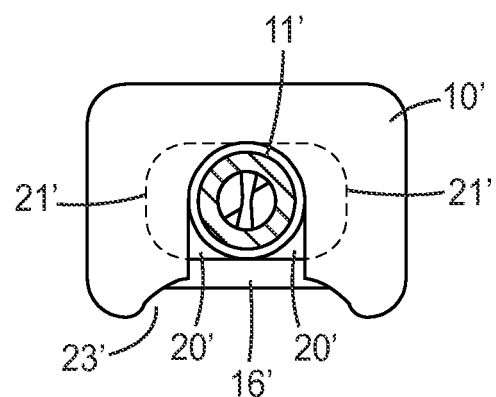
FIG. 7 is a front view of the device of FIG. 6 in the operative mode according an embodiment of the invention.

FIG. 7 is a front view of the device 10' in the operative mode with the cannula 11' positioned about 90° relative to the position in FIG. 6. The cannula 11' may be rotated into the position shown in FIG. 7 from the position shown in FIG. 6. Rotating the cannula 11' to bring the device 10' from the storage mode into the operative mode also causes the valve element 16' to rotate and therefore causes the valve to open the opening (not shown in this view) of the device.

As shown in FIG. 7 the window 23' in the area toward the front of the device 10' is laterally constricted with respect to the area of the window 23' toward the bottom side as shown in FIG. 6. The portions of the device constricting the window 23' in the position of the cannula 11' shown engage the retention elements 20' of the cannula 11' and therefore form retainers 21'. The retainers 21' retain the cannula 11' in one direction. Further the cannula 11' abuts in the inside of the device so that the cannula 11' is also retained in the opposite direction. The cannula 11' is further laterally restricted in the conduit of the device 10' so that the cannula 11' is entirely locked in the device 10'. Thus in the operative position a removal of the cannula 11' is disabled.

Although not shown in detail the embodiment shown in FIGS. 3 to 5 provides equivalent features and functions.

In the embodiments shown in FIGS. 3 to 7 the device is adapted such that the cannula can be mounted to the device by insertion of the cannula into the device with the backend leading. There are however further embodiments in which the cannula can be inserted into the device with the frontend leading. Such embodiments may particularly vary from the embodiments in FIGS. 3 to 7 due to the different principle of mounting the cannula, but may otherwise be equivalent or identical to the embodiments shown in FIGS. 3 to 7.

Figure 8:
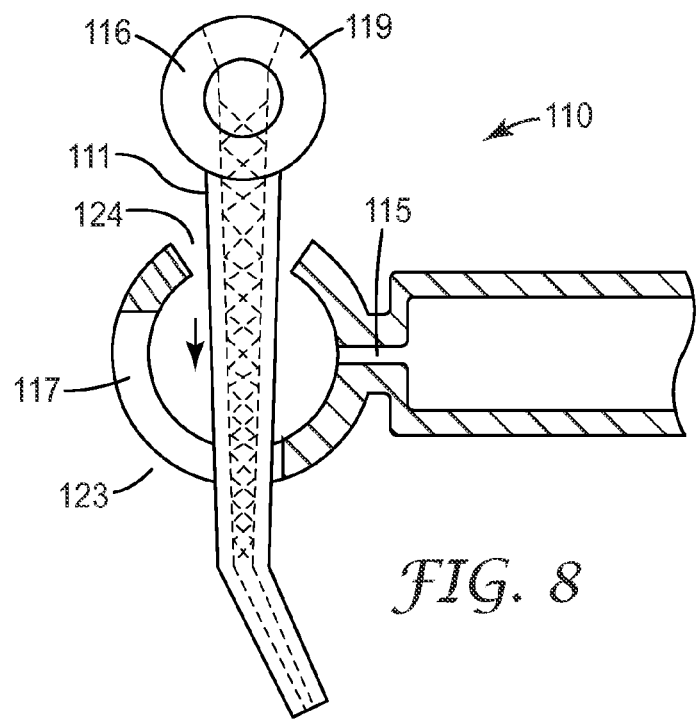
FIG. 8 is a partial cross-sectional view of a device with a cannula unconnected from the device according to another embodiment of the invention.

FIG. 8 shows a device 110 which is adapted such that the cannula 111 can be inserted with the frontend leading and the backend trailing. Such a configuration may generally be used as an alternative of the configuration as illustrated with the examples in FIGS. 3 to 7. The device 110 has a valve body 117 with a first window 123 and a second window 124. The first window 123 is sized so that the frontend of the cannula 111 can be passed through, but the backend 119 is retained by the valve body 117. The second window 124 is sized so that both, the frontend and the backend of the cannula 111 can be passed through. Therefore the cannula 111 can be inserted with the frontend leading in a direction from the second window 124 toward the first window 123, with the backend 119 finally arriving between the first and second windows 123, 124. In the embodiment shown in FIG. 8 the backend 119 of the cannula 111 forms the valve element 116. The valve element 116 in the example has a generally cylindrical outer shape, and the valve body 117 has a generally cylindrical inner shape. Thereby the valve element 116 and the valve body 117 are adapted to cooperate to form a valve in combination, in the example to form a rotary slide valve.

When the cannula 111 is received in the final position in the device 110 (not shown, but the cannula 111 in FIG. 8 moved further toward the bottom of the page), the device 111 is in the storage mode. In the storage mode the valve closes the outlet 115, and the cannula 111 is releasably received in the device 110. In the example shown, the backend 119 is slightly larger than the second window 124 so that the cannula 111, received in its final position is snap fit with the device 110. Thus the cannula 111 is releasably retained in the device 110 when in the storage mode. However, the skilled person will appreciate that to provide a loose fit a wider window 124 and/or a smaller backend 119 may be provided. A loose fit may facilitate insertion and removing of the cannula, for example.

Figure 9:
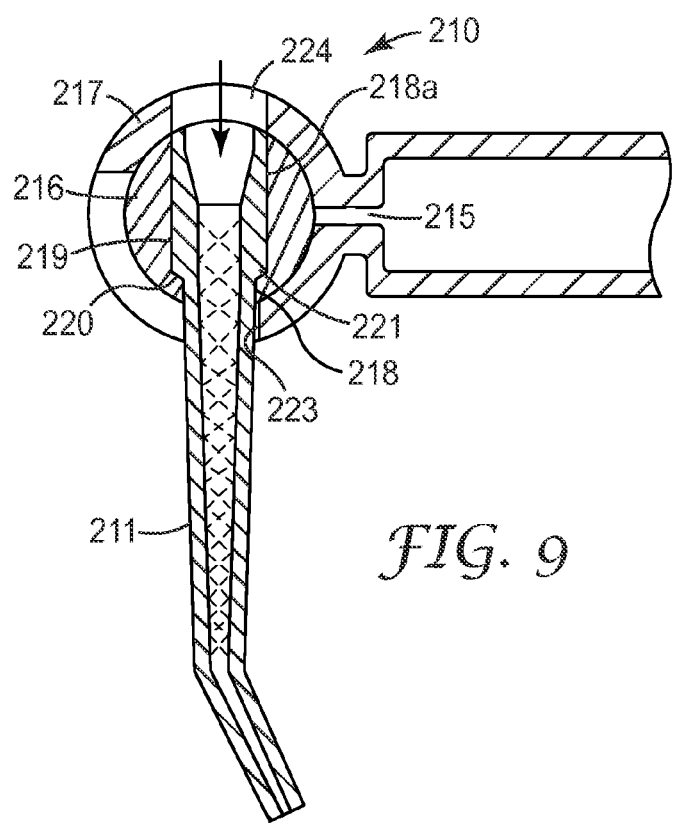
FIG. 9 is a partial cross-sectional view of a device with a cannula connected to the device and with the device in the storage mode according to a further embodiment of the invention.

FIG. 9 shows another example of a device which is adapted such that the cannula can be inserted in the device with the frontend leading and the backend trailing. The device 210 has a valve element 216 and a valve body 217 which together form a valve for opening and closing an outlet 215. The valve element has a conduit 218 with a widened portion 218a, and in the example is oriented with the widened portion 218a opening in a window 224 in the valve body. The window 224 in the example is sized to entirely open the widened portion 218a of the conduit 218 so that a backend 219 of a cannula 211 can be inserted in the widened portion 218a through window 224. The cannula 211 generally corresponds to the cannula 11 shown in FIGS. 3 to 5, and therefore has a backend 219 which has an annular rim forming a retaining element 220. The retaining element 220 may however also be formed by at least one or two wings, as described above.

The conduit on the opposite side of the widened portion 218a opens in a window 223 in the valve body 117. The conduit 218 is smaller than the widened portion 218a so that the transition between the conduit 218 and the widened portion 218a forms a step that acts as a retainer 221 for cooperation with the retaining element 220 of the cannula 211. In this example the retaining element 220 and the retainer 221 are in engagement when the device is in the storage mode as well as when the device is in the operative mode. However the cannula 211 in the storage mode of the device is releasably received such that the cannula 211 can be retracted from the device. In the operative mode of the device the cannula and thereby the valve element is positioned so that the opening of the widened portion 218a is covered by the valve body 217. In the operative position the cannula 219 abuts at the inner surface of the valve body 217 in one direction, is retained by the retainer 221 in the opposite direction and is restricted in the conduit laterally. Therefore in the operative position the cannula 211 is locked or unreleasably connected with the device.

Figure 10:
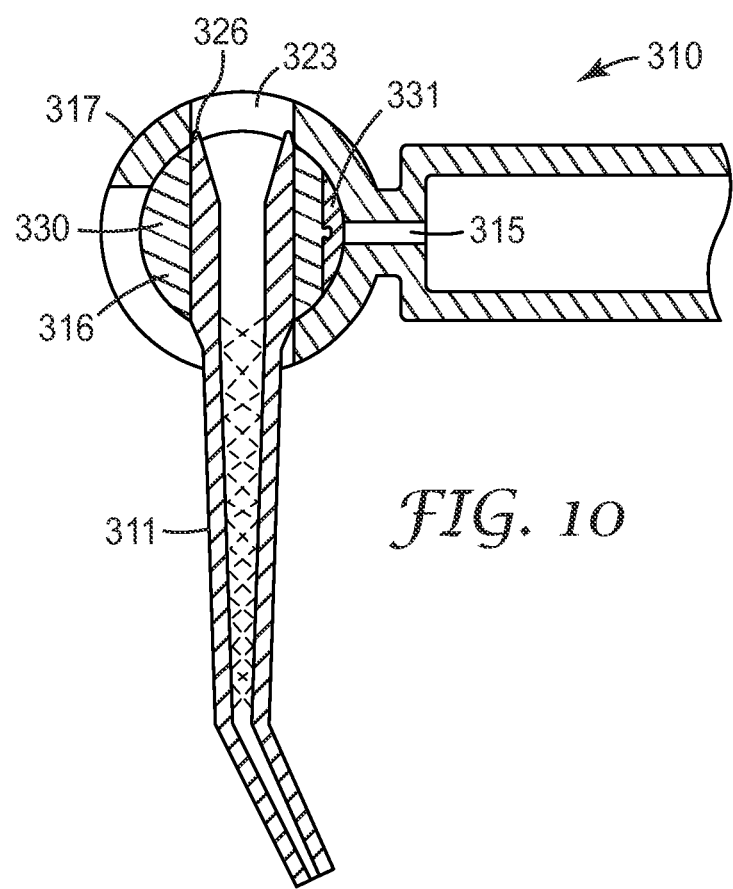
FIG. 10 is a partial cross-sectional view of a device in which the valve element has a sealing element according to another embodiment of the invention.

FIG. 10 shows a device 310 having a valve element 316 of at least two different materials. The valve element 316 may comprise a first material 330, for example providing an appropriate mechanical stability for the valve element, and may comprise a second material 331 which provides for example good sealing of the outlet. The second material 331 may be a relatively soft and/or elastic material, for example rubber or a thermoplastic elastomer. The example further shows a cannula 311 that has a seal 326. The seal 326 in the storage position of the device extends through the valve element 316 into a window 323 in the valve body 317. Therefore when the device is operated toward the operative position the seal is pressurized by the valve body. Thus in the operative position a good seal between the cannula and the outlet 315 may be achieved. An identical or similar configuration may also used with other embodiments described in this specification.

Figure 11:
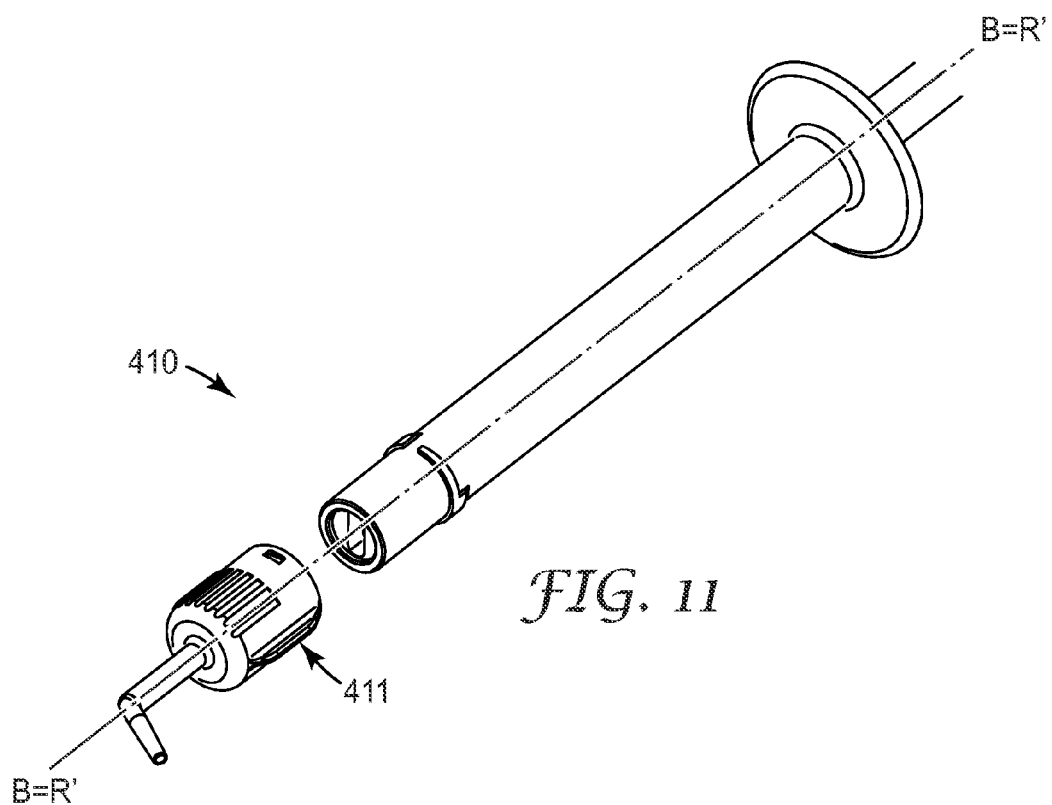
FIG. 11 is a perspective view of a dispensing device in the storage mode according to still a further embodiment of the invention.
Figure 12:
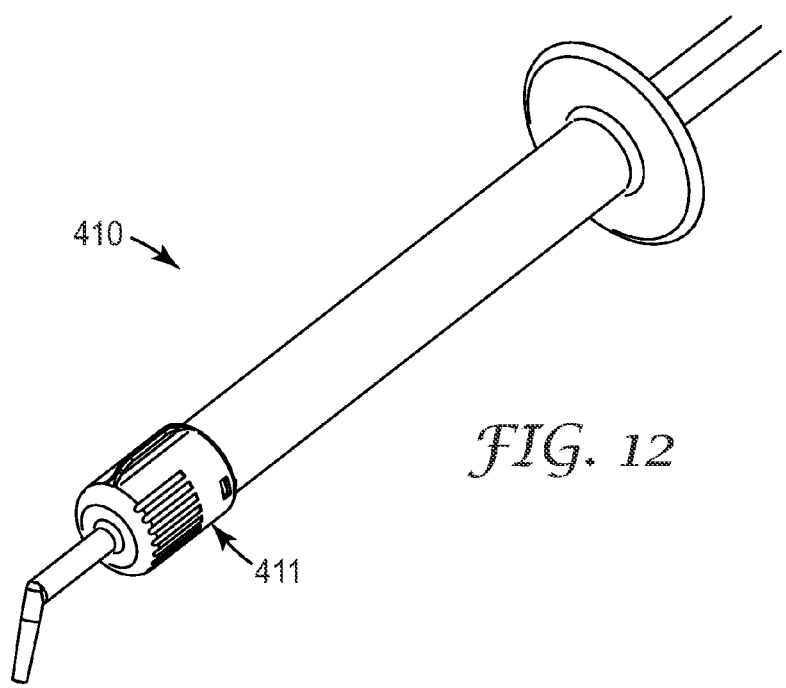
FIG. 12 is a perspective view of the dispensing device of FIG. 11 in the operative mode according to an embodiment of the invention.

FIGS. 11 and 12 show another embodiment of the invention which has a rotatable valve which varies from the embodiments shown in FIGS. 1 to 10 in that the rotation axis R' of the valve is generally parallel or in-line with a longitudinal axis B of the device.

FIG. 11 shows the device 410 in the storage mode in which the valve closes an outlet of the device so that substance contained in the device is sealed. A cannula 411 is shown separate from the device 410.

FIG. 12 shows the device 410 with the cannula 411 placed on the device 410.

Figure 13:
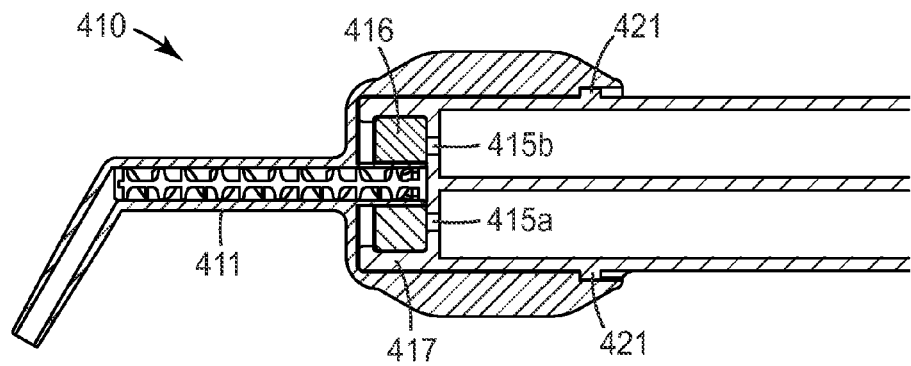
FIG. 13 is a partial cross-sectional view of the device of FIG. 11 in the storage mode according to an embodiment of the invention.

FIG. 13 shows a cross-section of the device 410 in the storage mode. The device 410 has a valve element 416 and a valve body 417 which in combination form a valve for outlets 415a, 415b. In the storage mode the valve closes the outlets 415a, 415b. The cannula 411 is received on the device 410. The device 410 has retainers 421, and the cannula has retention elements (not shown in this Figure) for engagement with the retainers 421. In the storage mode the retention elements 420 and the retainers 421 are disengaged as shown. Therefore in the storage mode the cannula 411 is releasable or removable from the device 410, although it is received on the device 410.

Figure 14:
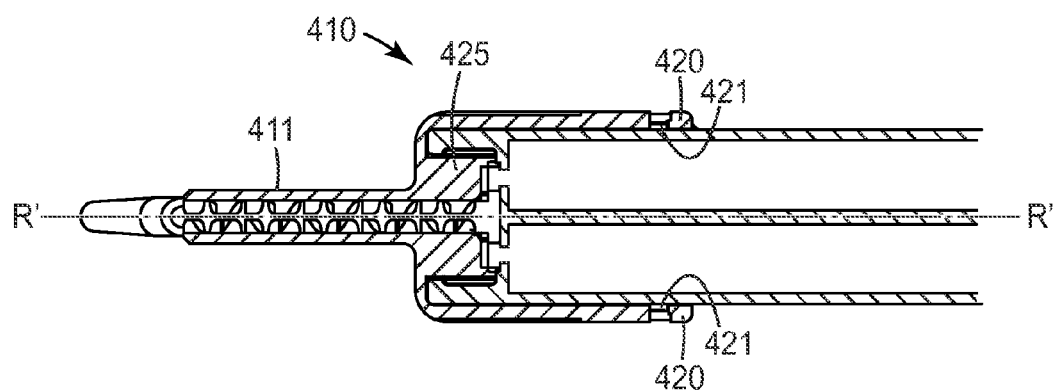
FIG. 14 is a partial cross-sectional view of the device of FIG. 11 in the operative mode according to an embodiment of the invention.

FIG. 14 shows the device 410 in the operative mode. In the operative mode the cannula 411 is positioned about 90° (other angles are possible) about the axis R' relative to the position in the storage mode (shown in FIG. 13). This can be achieved by rotating the cannula, for example by a user. A coupling is provided between the cannula 411 and the valve element (not visible in the view shown in FIG. 14) which may be brought in engagement as soon as the cannula 411 is received on the device so that subsequently moving the cannula causes the valve element to also rotate. Therefore rotating the cannula 411 to bring the device from the storage mode into the operative mode also causes the valve element to rotate and therefore causes the valve to open the openings of the device. A plurality of embodiments of a suitable coupling will be apparent for the skilled person. In the example shown the valve element has a slit (visible in FIG. 11) which can be engaged by a bar 425 (also indicated in FIG. 15) at the cannula 411. In the operative mode of the device 410 the retainers 421 and the retention elements 420 are further engaged with one another so that the cannula is locked on the device 410.

Figure 15:
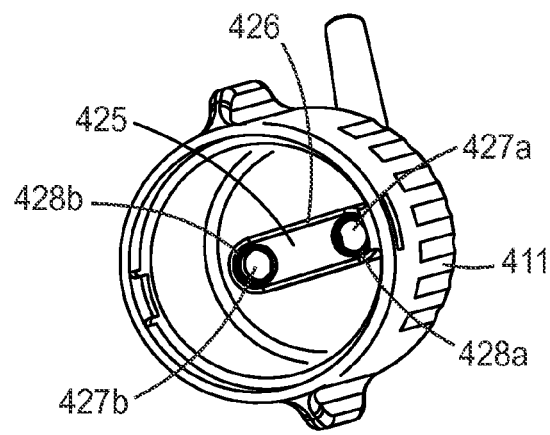
FIG. 15 is a perspective view of a cannula, for example for the device shown in FIG. 11, according to an embodiment of the invention.

FIG. 15 shows the backend of the cannula 411 in more detail. The bar 425 has a seal 426 for providing a seal between the cannula 411 and outlets of the device. The cannula 411 may further have inlets 427a, 427b for connecting with respective outlets of the device. Each of the inlets 427a, 427b may be surrounded by inlet seals 428a, 428b, respectively. The inlet seals 428a, 428b preferably prevent substances dispensed from outlets of the device, for example different components for forming a hardenable material, to merge in an area the cannula contacts the device. Substances dispensed from outlets of the device may accordingly only merge within the cannula. Therefore merged substances may be removed effectively together with replacing the cannula. For example portions of hardened material may be removed before a fresh cannula is placed on the device so that the device can be further used.

Figure 16:
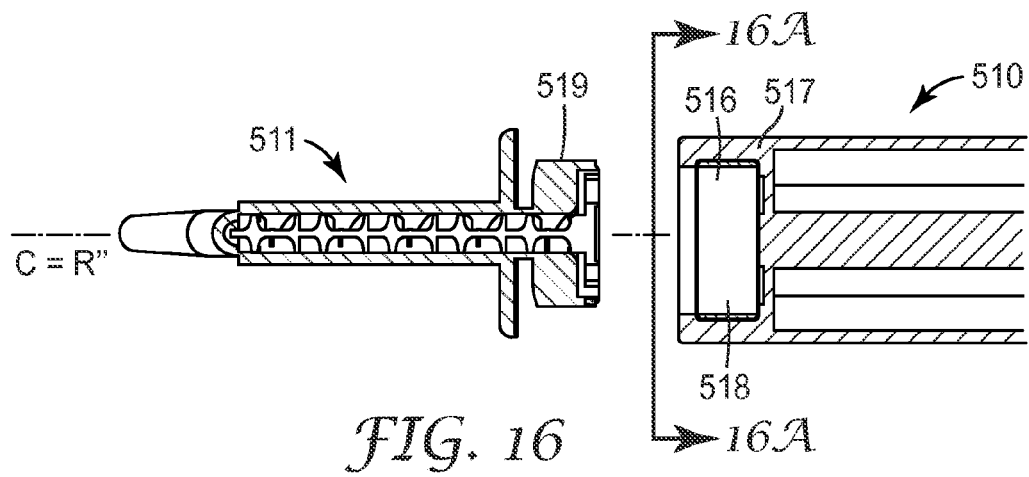
FIG. 16 is a partial cross-sectional view of a device with a cannula disconnected from the device according to a further embodiment of the invention.
Figure 17:
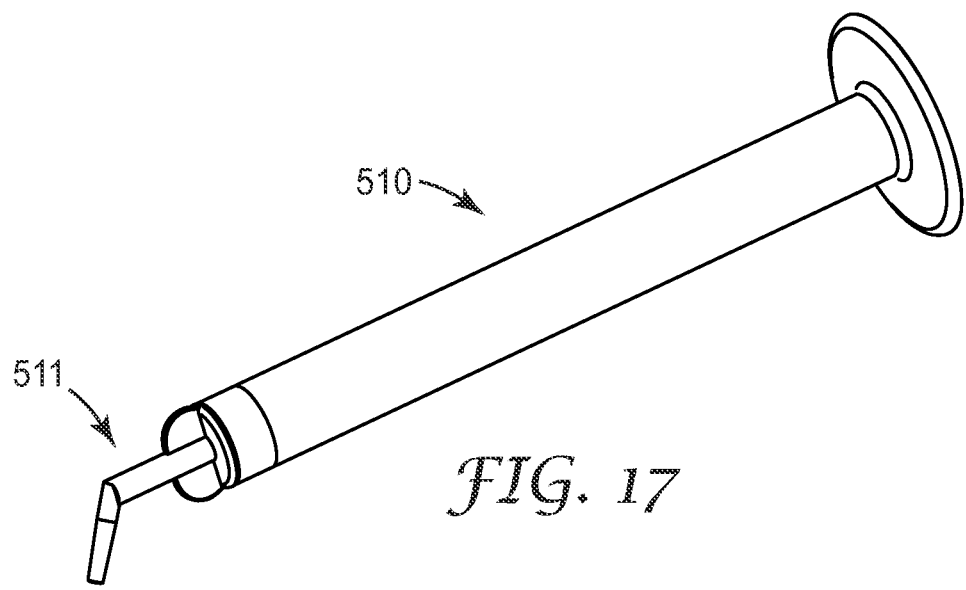
FIG. 17 is a partial cross-sectional view of a device with a cannula placed on the device according to an embodiment of the invention.

FIGS. 16 and 17 show another example having a valve that has a rotation axis R'' which is generally parallel or in-line with a longitudinal axis C of the device. FIG. 16 shows the device 510 and a cannula 511 when disassembled, and FIG. 17 shows the device 510 with the cannula 511 placed on the device 510. The device 510 comprises a valve element 516, and a valve body 517. The valve element has a conduit 518 for receiving a backend 519 of the cannula 511. Also this embodiment can be switched between a storage mode and an operative mode by rotating the cannula 511 around the axis R'' when placed on the device. In the storage mode the cannula 511 is releasable from the device 510, and in the operative mode the device may be used to dispense a substance from the device 510 through the cannula 511. After use the device may be switched back to storage mode, and the cannula may be left placed on the device until it is replaced by a new cannula for the next use.

Figure 16A:
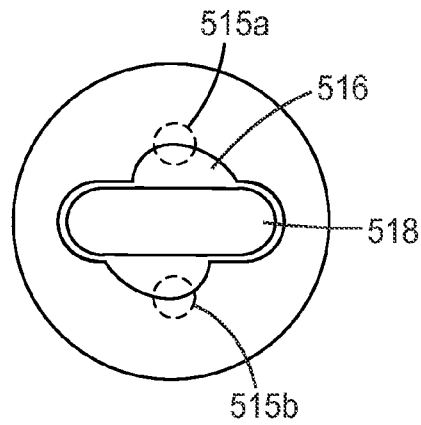
FIG. 16A is a detail view onto a front end of the device shown in FIG. 16.

FIG. 16A shows in more detail a front end of the device in the storage position. The valve element 516 closes outlets 515a, 515b (hidden by the valve element). In the storage position shown the conduit 518 is accessible for receiving the backend (shown in FIG. 16 as reference no. 519) of the cannula.

Figure 18:
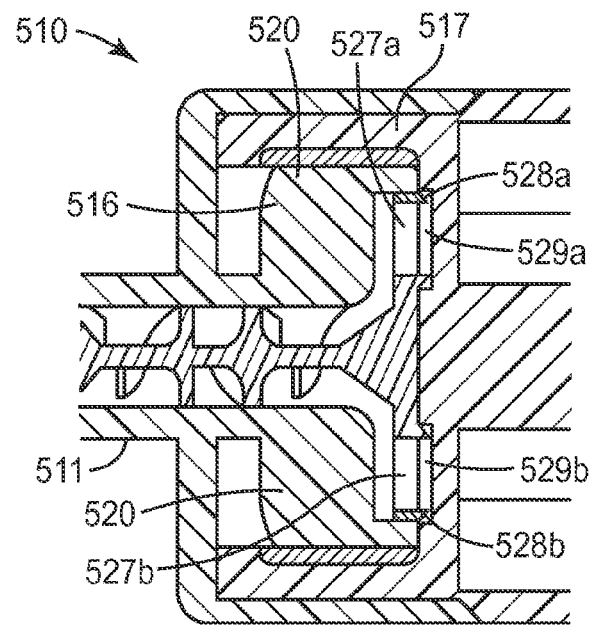
FIG. 18 is a partial cross-sectional view of the device of FIG. 17 in the storage mode according to an embodiment of the invention.

FIG. 18 shows a cross-section of the device 510 in the storage mode. The valve element 516 and the valve body 517 in combination form a valve for outlets (shown as references 515a, 515b in FIG. 19). In the storage mode the valve closes the outlets (not visible in the view of FIG. 18). The device may have, as shown, recesses 529a, 529b in which seals 528a, 528b around inlets 527a, 527b into the cannula 511 may be received.

The recesses 529a, 529b may allow the seals 528a, 528b to project from the cannula 511 in the storage position, and in the operative position (FIG. 19) the seals may be compressed. Therefore a good seal between the cannula and the device may be achieved. On the other hand, when the seal is moved back from the operative position to the storage position the seals may wipe off substance from the outlets of the device and may disconnect from the device in the recesses. The recesses thus may be kept substantially free of substances. Therefore cross-contamination between different substances contained in the device may be prevented.

The device 510 has retainers (shown in FIG. 19 as reference no. 521), and the cannula 511 has retention elements 520 for engagement with the retainers. In the storage mode the retention elements 520 and the retainers are disengaged as shown. Therefore in the storage mode the cannula 511 is releasable from the device 510, although it is received on the device 510.

Figure 19:
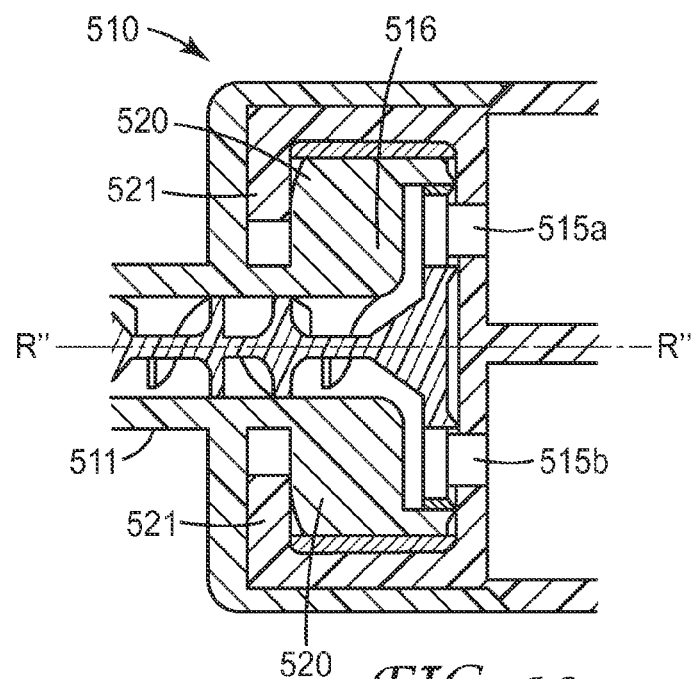
FIG. 19 is a partial cross-sectional view of the device of FIG. 17 in the operative mode according to an embodiment of the invention.

FIG. 19 shows the device 510 in the operative mode. In the operative mode the cannula 511 is positioned about 90 degrees (other angles are possible) about the axis R" relative to the position in the storage mode (shown in FIG. 18). This can be achieved by rotating the cannula, for example by a user. In the FIG. 19 the device is shown rotated by about 90 degrees about axis R". Because the valve element 516 is engaged with the cannula 511 moving the cannula 511 causes the valve element 416 to rotate. Therefore rotating the cannula to bring the device from the storage mode into the operative mode also causes the valve element to rotate and therefore causes the valve to open the openings 515a, 515b of the device. In the operative mode of the device 510 the retainers 521 and the retention elements 520 are further engaged so that the cannula is locked on the device.

The invention has now been described by way of examples. The skilled person will appreciate further embodiments in which the features described are combined in a different manner. Further the features may be replaced by equivalent features to achieve an equivalent device. It is pointed out that features described for a certain embodiment may be used in any of the other embodiment as appropriate.

The embodiments disclosed herein may further have certain features in common. For example the cannula may comprise a static mixer. The device may have one, two or more chambers for containing a substance or components of a substance, and each of such chambers may comprise a piston for extruding the substance from the piston.

The device may further generally comprise at least one fingerplate. The piston may comprise a corresponding pressure plate so that the piston can be urged into the device by forcing the fingerplate and the pressure plate toward one another. Two (or more) pistons may be combined to form a plunger that further comprises a common pressure plate.

The device, the cannula, the valve element, the valve body and the piston or plunger may be made of plastic. Suitable plastic materials may be Polypropylene, Polyethylene, Polyoxymethylene, Polyamide, Polyethylene Terephthalate, Polycarbonate, Polybutadiene Terephthalate. Such plastic materials may be combined as appropriate. An exemplary combination is:
Device: Polypropylene,
Cannula: Polycarbonate,
Valve element: Polyoxymethylene,
Valve body: Polypropylene, and
Piston or plunger: Polyoxymethylene.

A device according to the invention may be adapted to contain a total fill volume of between about 0.5 ml to about 10 ml.

The invention claimed is:

1. A dispensing device for a dental substance, comprising:
a chamber having a longitudinal axis that opens into an outlet;
a piston, where the piston can move along the longitudinal axis through the chamber to urge the dental substance toward the outlet;
a valve having a valve body and a valve element that move relative to each other for opening and closing the outlet, and wherein the valve element defines a conduit being adapted for receiving a cannula for connection with the outlet,
the device being operable between a storage mode and an operative mode,
wherein the device is further adapted such that activating the operative mode causes locking the cannula, when it is present, in the device, and rotating the cannula causes the valve to open the outlet wherein the cannula, when present, extends entirely through the conduit of the valve element to form a seal around the outlet; and
wherein the device is adapted such that activating the storage mode causes
the valve to close the outlet, and releasing the cannula, when it is present, from the device.

2. The dispensing device of claim 1, wherein the valve body comprises the outlet and the valve element comprises a sealing surface and the valve body and the valve element are movable relative to one another to a closed position in which the sealing surface seals the outlet so that the outlet is closed.

3. The dispensing device of claim 2, wherein the valve element has a generally cylindrical outer surface, and the valve body has a generally cylindrical inner surface, with the outer surface of the valve element and the inner surface of the valve body being mated with one another, such that the valve body and the valve element are rotatable relative to one another around a rotation axis.

4. The dispensing device of claim 3, wherein the rotation axis is generally parallel to or aligned with the longitudinal axis of the device.

5. The dispensing device of claim 3, wherein the sealing surface is arranged on a face side of the valve element which is generally transverse to the rotation axis.

6. The dispensing device of claim 1, comprising the cannula.

7. The dispensing device of claim 6, comprising a container, wherein the container has a retainer, and wherein the cannula has a retention element which is adapted to cooperate with the retainer for locking the cannula in the device.

8. The dispensing device of claim 7, wherein the retention element of the cannula is formed by an annular rim adjacent the backend of the cannula or by at least one wing projecting sideward from the cannula.

9. The dispensing device of claim 6, wherein the cannula comprises a static mixer.

10. The dispensing device of claim 7, wherein the container has two chambers, each for receiving at least a component of a dental substance, and wherein the dispensing device has a plunger that comprises two pistons being receivable in the chambers, respectively, for extruding the dental substance from the chamber.

11. The dispensing device of claim 6, wherein the cannula has a socket for receiving a front end of the container.

12. The dispensing device of claim 1, containing a dental substance selected from among a dental filling material, a dental impression material, a dental sealant, and a dental adhesive.

13. A dispensing device, comprising:
a chamber having a longitudinal axis that opens into an outlet;
a piston, where the piston can move along the longitudinal axis through the chamber to urge a dental substance toward the outlet;
a valve having a valve body and a valve element that move relative to each other for opening and closing the outlet, the valve comprising a conduit, wherein the conduit has a widened portion; and
a cannula for connection with the outlet, wherein the device is further adapted such that activating the operative mode causes locking the cannula, when it is present, in the device, and rotating the cannula causes the valve to open the outlet, wherein the cannula, when present, extends entirely through the conduit of the valve element to form a seal around the outlet;

wherein the device is adapted such that activating the storage mode causes the valve to close the outlet, and releasing the cannula, when it is present, from the device.

14. The dispensing device of claim 13, wherein the cannula further comprises a seal between the outlet and the cannula.

15. The dispensing device of claim 13, wherein the conduit further comprises a step provided by a transition between the conduit and the widened portion, wherein the step acts as a retainer to lock the cannula.

16. The dispensing device of claim 13, wherein the dispensing device comprises a container for receiving the dental substance and wherein the container further comprises a retainer, and wherein the cannula includes a retention element to cooperate with the retainer for locking the cannula in the device.

* * * * *